(12) United States Patent
Pinchuk et al.

(10) Patent No.: US 8,585,940 B2
(45) Date of Patent: Nov. 19, 2013

(54) OCULAR LENS

(75) Inventors: Leonard Pinchuk, Miami, FL (US); Yonghua Zhou, Miami, FL (US); Yongmoon Kwon, Weston, FL (US); Yasushi Pedro Kato, Weston, FL (US)

(73) Assignee: Innolene LLC, Miami, FL (US)

( * ) Notice: Subject to any disclaimer, the term of this patent is extended or adjusted under 35 U.S.C. 154(b) by 640 days.

(21) Appl. No.: 12/776,138

(22) Filed: May 7, 2010

(65) Prior Publication Data
US 2010/0283164 A1 Nov. 11, 2010

Related U.S. Application Data

(60) Provisional application No. 61/176,527, filed on May 8, 2009.

(51) Int. Cl.
*B29D 11/00* (2006.01)

(52) U.S. Cl.
USPC ............................. 264/1.1; 264/2.2; 264/2.6

(58) Field of Classification Search
USPC .............. 264/1.1, 1.32, 2.6, 2.7, 2.2; 425/808
See application file for complete search history.

(56) References Cited

U.S. PATENT DOCUMENTS

| | | | |
|---|---|---|---|
| 4,254,509 A | 3/1981 | Tennant | |
| 4,708,994 A | 11/1987 | Wong | |
| 4,758,631 A | 7/1988 | Kennedy et al. | |
| 4,932,966 A | 6/1990 | Christie et al. | |
| 5,489,302 A | 2/1996 | Skottun | |
| 6,117,171 A | 9/2000 | Skottun | |
| 6,299,641 B1 | 10/2001 | Woods | |
| 6,406,494 B1 | 6/2002 | Laguette et al. | |
| 7,344,731 B2 | 3/2008 | Lai et al. | |
| 2005/0125059 A1 | 6/2005 | Pinchuk et al. | |
| 2005/0187414 A1 | 8/2005 | Faust et al. | |
| 2005/0200033 A1* | 9/2005 | Kadota et al. | ............... 264/1.31 |
| 2009/0124773 A1 | 5/2009 | Zhou et al. | |

OTHER PUBLICATIONS

Relative Reactivity of C4 Olefins toward the Polyisobutylene Cation, P. De and R. Faust, Macromolecules, vol. 39 (2006) pp. 6861-6870.
Living carbocationic polymerization XII. Telechelic polyisobutylenes by a sterically hindered bifunctional initiator. Wang B, Mishra MK, Kennedy JP., Polym. Bull. 1987;17:205-11.
Living carbocationic polymerization VIII. Telechelic polyisobutylenes by the MeO(CH2)2C-p-05H4-C(CH3)2 Ome/BCI3 initiating system. Mishra MK, Kennedy JP., Polym. Bull. 1987 17:7-13.

* cited by examiner

*Primary Examiner* — Mathieu D. Vargot
(74) *Attorney, Agent, or Firm* — Gordon & Jacobson, PC (57) ABSTRACT

A method of making an ocular lens device (and resulting lens device) from a polyolefin copolymer material having a crosslinking component, wherein the material is processed to remove unwanted reaction byproducts that can contribute to reduced transparency of the polyolefin copolymer material in the ocular environment of the eye.

33 Claims, 5 Drawing Sheets

OCULAR LENS

CROSS-REFERENCE TO RELATED APPLICATIONS

The present application claims priority from U.S. Provisional Pat. Appl. No. 61/176,527, filed on May 8, 2009, herein incorporated by reference in its entirety.

BACKGROUND OF THE INVENTION

1. Field of the Invention

This invention relates broadly to ocular lens devices. More particularly, this invention relates to intraocular lens devices that are surgically implanted within the capsular bag of a human eye as well as other ocular lens devices.

2. State of the Art

Figure 1:
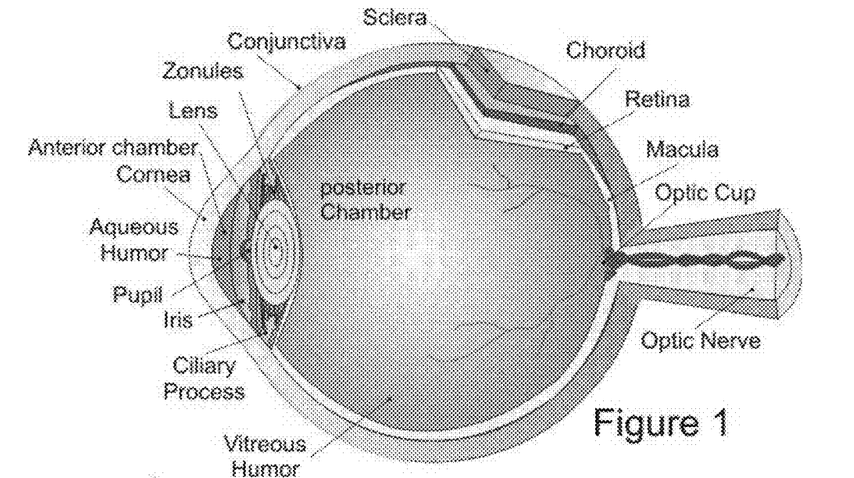
FIG. 1 is a schematic illustration of the anatomy of the human eye.

Looking at FIG. 1, the natural lens of a human eye is a transparent crystalline body, which is contained within a capsular bag located behind the iris and in front of the vitreous cavity in a region known as the posterior chamber. The capsular bag (or lens capsule) is attached on all sides by fibers, called zonules, to a muscular ciliary body (or process). At its rear, the vitreous cavity, which is filled with a gel, further includes the retina, on which light rays passing through the lens are focused.

Figure 2:
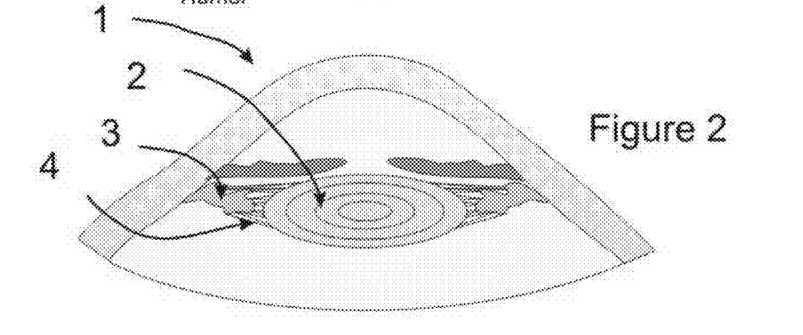
FIGS. 2 and 3 are schematic illustrations showing the accommodation function provided by the natural crystalline lens of the human eye.
Figure 3:
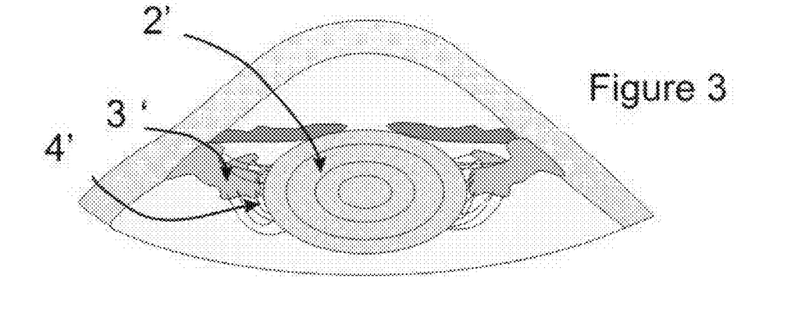

Although not to he held to one theory or another, the subject of this invention will be described according to what is know to those skilled in the art as the Helmholtz theory of accommodation (Helmholtz Theory). The Helmholtz Theory states that the lens will change in shape as the lens capsule stretches horizontally and relaxes back to its more rounder geometry. As shown in FIG. 2, when the ciliary muscles are relaxed, the Zonules are under tension causing the lens to stretch horizontally to see far distances. Conversely, as is shown in FIG. 3, when the ciliary muscles are contracted, the Zonules are relaxed and the lens assumes a more rounded shape to enable near vision.

Contraction and relaxation of the ciliary bodies (FIGS. 2 and 3) changes the shape of the bag and of the natural lens therein, thereby enabling the eye to focus light rays on the retina originating from objects at various distances. The ability of the lens to focus both far and near is referred to as "accommodation". The human eye is subject to a variety of disorders which degrade, or totally destroy, the ability of the eye to function properly. One of the more common of these disorders involves progressive clouding of the crystalline lens matrix resulting in the formation of what is referred to as a cataract. Another is the general hardening of the lens which limits the amount of accommodation of the lens that the zonules and ciliary bodies can impart to the them. The progressive loss of accommodation is called "presbyopia."

It is common practice to cure a cataract by surgically removing the clouded crystalline lens and implanting an artificial intraocular lens in the eye to replace the natural lens. Various types of intraocular lenses having the capability of altering their refractive power have been suggested in an effort to duplicate the performance of the natural lens within the eye. Such accommodating intraocular lenses, as they are known in the art, have a variety of designs directed to enable the patient to focus on, and thereby clearly see, objects located at a plurality of distances. Examples may be found in such publications as U.S. Pat. Nos. 4,254,509; 4,932,966; 6,299,641; and 6,406,494.

U.S. Pat. No. 5,489,302 discloses an accommodating intraocular lens for implantation in the posterior chamber of the eye. This lens comprises a short tubular rigid frame and transparent and resilient membrane attached thereto at its bases. The frame and the membranes confine a sealed space filled with a gas. The frame includes flexible regions attached via haptics to the posterior capsule. Upon stretching of the capsule by the eye's ciliary muscles, the flexible regions are pulled apart, thereby increasing the volume and decreasing the pressure within the sealed space. This changes the curvature of the membranes and accordingly, the refractive power of the lens.

U.S. Pat. No. 6,117,171 discloses an accommodating intraocular lens which is contained inside an encapsulating rigid shell so as to make it substantially insensitive to changes in the intraocular environment. The lens is adapted to be implanted within the posterior capsule and comprises a flexible transparent membrane, which divides the interior of the intraocular lens into separate front and rear spaces, each filled with a fluid having a different refractive index. The periphery of the rear space is attached to haptics, which are in turn attached to the posterior capsule. Upon stretching of the capsule by the eye's ciliary muscles, the haptics and hence this periphery is twisted apart to increase the volume of rear space and changes the pressure difference between the spaces. As a result, the curvature of the membrane and accordingly, the refractive power of the lens changes.

After surgical implantation of the intraocular lens in the capsular bag of the eye, active epithelial cells on the posterior side of the anterior capsule rim of the capsular bag cause fusion of the rim to the elastic posterior capsule wall by fibrosis. This fibrosis occurs about the haptics of the IOL in such a way that the haptics are effectively "shrink-wrapped" by the fibrous tissue in such a way as to form radial pockets in the fibrous tissue. These pockets contain the haptics with their outer ends positioned within the outer perimeter of the capsular bag. The lens is thereby fixated with the capsular bag with the lens optic aligned with the optical axis of the eye.

With time, depending on the rearward pressure of the intraocular lens on the posterior capsule wall as well as other factors (such as lens material, lens geometry, angulation, sharpness, wrinkles in the posterior capsule wall, etc), epithelium cells can migrate between the posterior capsule wall and the lens and reside and multiply in these spaces. Excessive build up of the cells in this area can lead to opacification of the optic. This opacification, commonly referred to as posterior capsule opacification (PCO), causes clouding of vision and can lead to blurring and possibly total vision loss. The process of PCO is slow and clinical changes often take one to two years to become apparent. PCO is typically treated by YAG laser capsulotomy. However, in terms of health economics, PCO is very expensive to treat.

SUMMARY OF THE INVENTION

In accord with one embodiment of the invention, an improved method of making an ocular lens device (and resulting lens device) is provided. A polyolefin copolymer material having a crosslinking component is processed to remove unwanted reaction byproducts that can contribute to reduced transparency of the polyolefin copolymer material in the ocular environment of the eye. A refractive optics structure is formed from the processed polyolefin copolymer material. The forming involves thermal activation of the crosslinking component of the polyolefin copolymer material in order to crosslink the polyolefin copolymer material.

The processing of the polyolefin copolymer material involves dissolving polyolefin copolymer in a solution (preferably a hexane solution) and filtering the solution by multi-stage microfiltration. In the preferred embodiment, the multistage microfiltration includes a plurality of stages each with a filter membrane (more preferably realized from PTFE) having a specified pore size in a range between 0.1 µm to 0.3 µm (more preferably 0.2 µm).

The processing of the polyolefin copolymer material also involves repeated precipitation of polyolefin copolymer material before the multi-stage microfiltration. In the preferred embodiment, the precipitation of polyolefin copolymer material is carried out in a solution including ethyl acetate.

The unwanted reaction byproducts removed by the processing of the polyolefin copolymer material preferably include homopolymers of a crosslinking component of the polyolefin copolymer material;

homopolymers of a glassy component of the polyolefin copolymer material; and water-soluble and non-water-soluble particles of a predetermined size corresponding to the characteristic wavelength range of visible light as well as water-soluble and non-water-soluble particles greater than said predetermined size.

It can also remove other unwanted reaction byproducts.

In the preferred embodiment, the polyolefin copolymer material comprises

A) a plurality of constitutional units that include at least one cationically polymerized polymerizable isoolefin selected from the group consisting of isobutylene, 2-methyl-1-butene, 2-methyl-1-pentene, 2-methyl-1-hexene, and combinations thereof;

B) a plurality of constitutional units that include at least one cationically polymerized polymerizable olefin monomer having a pendant benzocyclobutene (BCB) group; and optionally C) a plurality of constitutional units that include at least one glass-forming monomer.

Isobutylene is more preferred for the isoolefin of A). 4-vinylbenzocyclobutene or 2-(4-benzocyclobutenyl)-propene is more preferred for the olefin monomer having a pendant BCB group of B). The glass-forming monomer of C) can be selected from the group consisting of styrene, indene, α-methylstyrene, p-tert-butylstyrene, p-chlorostyrene, p-methoxystyrene, p-tert-butoxystyrene, p-hydroxystyrene, norbornene, and combinations thereof.

The polyolefin copolymer material is preferably synthesized using tricumyl ether as an initiator molecule and isobutylene that is randomly polymerized with 4-vinylbenzocyclobutene.

Accommodating and non-accommodating intraocular lens as well as other ocular devices can be realized from the methodology described herein.

Additional objects and advantages of the invention will become apparent to those skilled in the art upon reference to the detailed description taken in conjunction with the provided figures.

BRIEF DESCRIPTION OF THE DRAWINGS

FIG. 4 is a schematic perspective view of an exemplary intraocular lens device in accordance with the present invention.

FIGS. 5 to 11b are schematic illustrations of exemplary intraocular lens devices in accordance with the present invention.

DETAILED DESCRIPTION OF THE PREFERRED EMBODIMENTS

In accordance with the present invention, an accommodating intraocular lens is provided that is made from a very resilient and stretchy material with a low modulus of elasticity. In its simplest form, shown in FIG. 4, the lens 6 consists of a central optic 7 and a radial haptic 8. The optic 7 and radial haptic 8 can be formed into many different shapes which are shown in cross-section in FIGS. 5 to 11b.

Figures 4, 5:
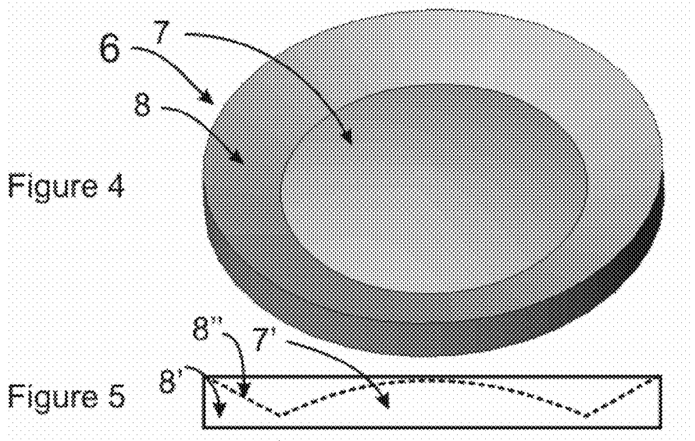

FIG. 5 shows a cross-section of convex-plano lens 6 with optic 7' and haptic 8'. Haptic 8' has a sloped surface 8" extending from the minor thickness of the optic to the upper periphery of the haptic.

Figure 6:
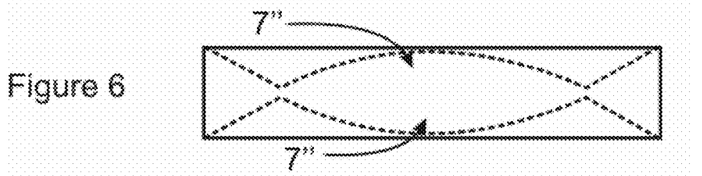

FIG. 6 shows a cross-section of a convex-convex lens with convex optics 7".

Figure 7:
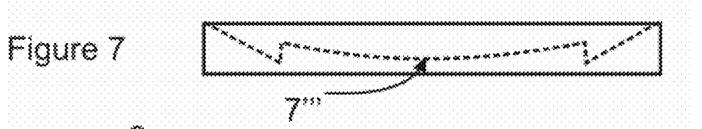

FIG. 7 shows a cross-section of a concave-plano lens with a concave optic 7'''.

Figure 8:
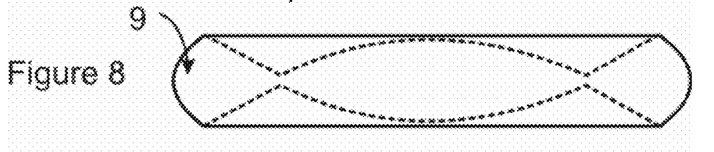

FIG. 8 is similar to the convex-convex lens in FIG. 6; however the edge of the haptic is filleted at 9.

Figure 9:
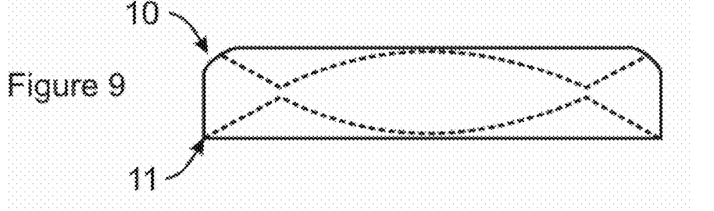

FIG. 9 is also a convex-convex lens; however, the upper corner 10 of the haptic is filleted and the lower corner 11 is sharp.

Figure 10:
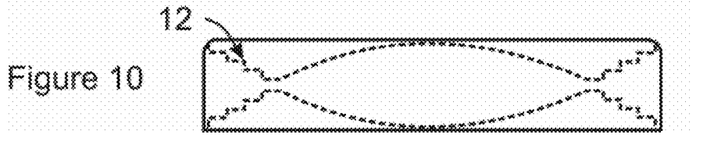

FIG. 10 is also a convex-convex lens however the angled haptic 12 is stepped.

Figure 11A:
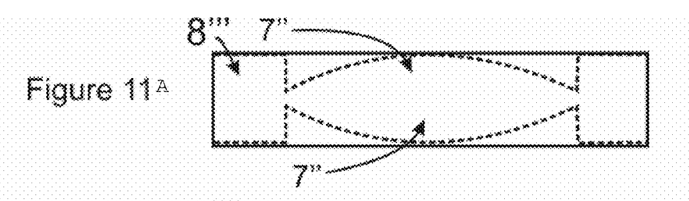

FIG. 11a is also convex-convex; however the haptic 8''' is square or rectangular in shape.

Figure 11B:
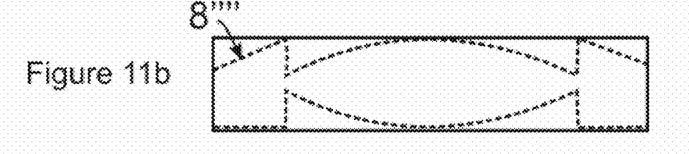

FIG. 11b is similar to FIG. 11a, but the haptic 8'''' is sloped downward. Note that it is shown only sloped down on the upper side. However, it can be sloped downward on both sides if desired.

Figure 12:
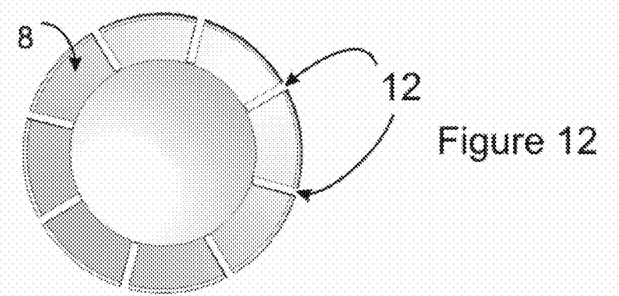
FIGS. 12, 13 and 14 are schematic illustrations of an exemplary lens device with a slotted haptic disposed about the circumference of the lens.
Figures 13, 14:
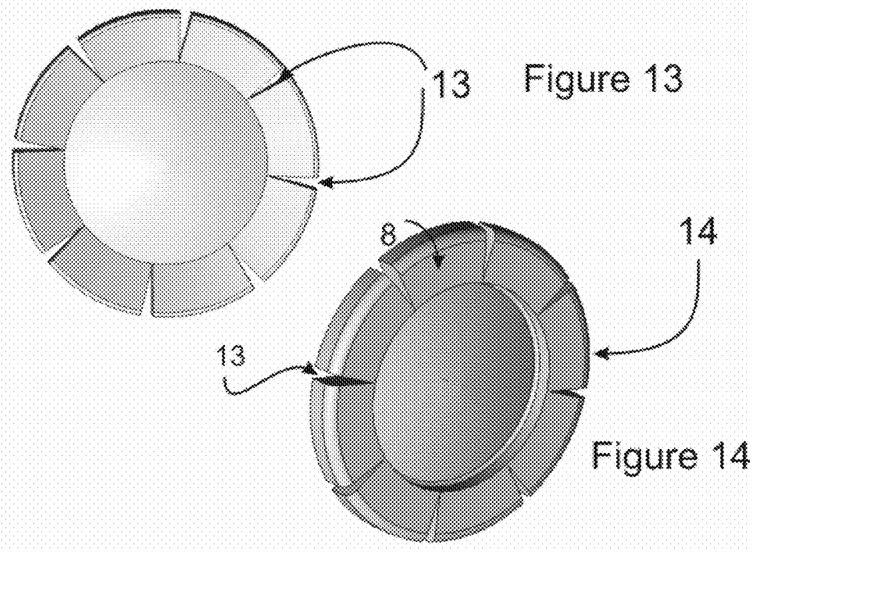

Turning now to FIG. 12, the haptic area 8 has a plurality of radially oriented slots 12 located around the circumference of the lens. FIG. 13 is similar; however the slots are wedge-shaped 13. The cross-section of FIGS. 12 and 13 are defined in FIG. 5; that is, it is convex-plano. FIG. 14 has wedged slots 13; however, the haptic 8 area in cross-section is square or rectangular as is shown in FIG. 11a.

Figure 15:
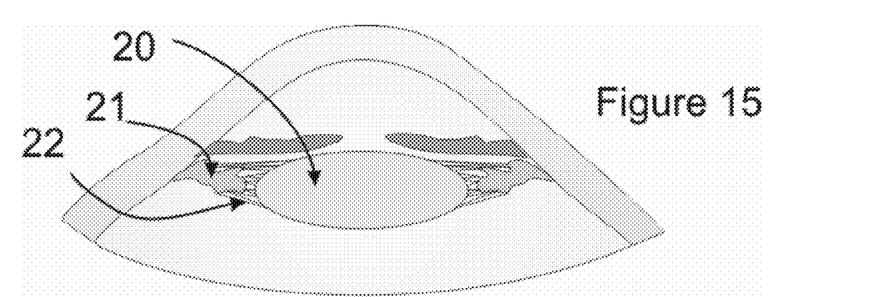
FIGS. 15 and 16 are schematic illustration of a surgical method for implanting an intraocular lens device of the present invention into the eye.
Figure 16:
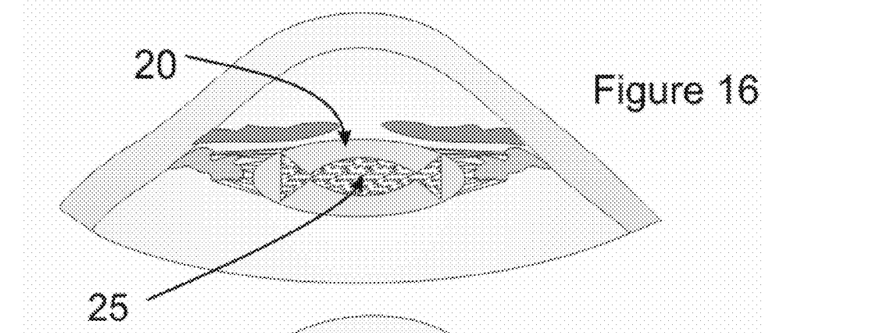

The intraocular lens of the present invention as described above is surgically implanted into the eye as follows. As shown in FIG. 15, the nucleus of lens capsule 20 is removed by phacoemulsification, which is well-known in the art. A lens 25 of any cross-sectional design shown in FIGS. 5-14 is inserted either with a forceps or with an inserter, which is also well-known in the art, in the empty lens capsule 20. As shown in FIG. 16, the diameter of the lens 25 is such that it fits somewhat snugly in the lens capsule 20 and remains relatively centered. Note that the lens 25 can also have whisker-type haptics to immediately center the lens; however, they may not be necessary if the capsule and lens are sized correctly. In addition, the lens 25 can have both whisker-type haptics protruding from the annular haptics 8 (not shown) to help center the lens for varying size lens capsules.

Figure 17:
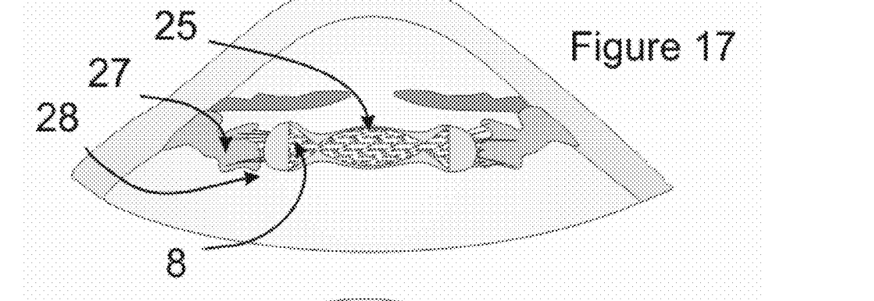
FIGS. 17 and 18 are schematic illustrations showing the accommodation function provided by the intraocular lens device implanted into the eye according to the method of FIGS. 15 and 16.
Figure 18:
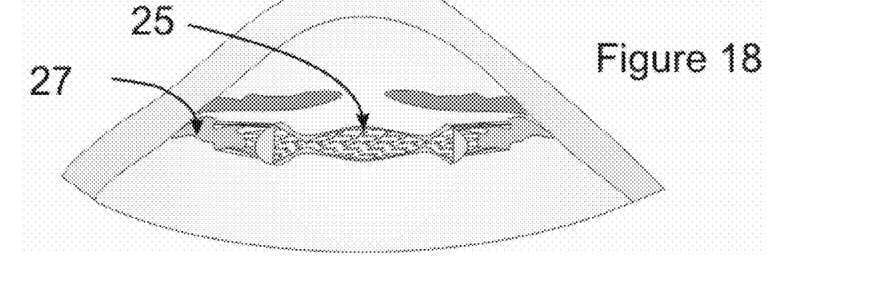

As shown in FIGS. 17 and 18, with time, the lens capsule 20 shrinks around, and envelopes the lens. The "shrink wrap" follows the contours of the lens. The shrink wrap allows the lens capsule to engage and "hold onto" the haptic area 8, such that when the ciliary muscles 27 relax and pull the zonules 28, it causes the lens capsule which is engaged with the haptic to pull the haptics radially outward. As the haptics are thicker than the lens (especially clear in FIG. 11), the tension in the haptics causes the lens to stretch and thereby change its radius of curvature and focus at a different focal spot. In other words, the change in radius of curvature manifests as a change in diopter and allows the lens to accommodate using the natural ciliary muscles of the eye.

Returning now to FIG. 4, here the haptic is one piece. If a single piece haptic is pulled outward radially, the haptic will have to change its circumference which will require large forces. As shown in FIGS. 12, 13 and 14, if the haptic is slotted or if wedge-shaped slots are included, the force of elongating the haptics is minimized and all of the forces from the ciliary muscles are directed towards stretching the central optic 7. Similarly, if the haptics are pushed, it can cause the lens to compress with a resultant lesser radius of curvature. FIGS. 11a and 11b show preferred cross-sectional designs where the haptic is block or rectangular-shaped in cross-section. FIG. 14 is an angled design of this preferred embodiment with wedge-shaped 13 slots.

A problem associated with current intraocular lenses is the presence and proliferation of lens epithelial cells which can grow between the lens and the lens capsule. This proliferation can render the posterior surface of the lens capsule opaque. This phenomenon is called Posterior Capsule Opacification or PCO. PCO is delayed by using a square edge on the optic or haptic as is shown in FIGS. 5, 6, 7, 11a and 11b. FIGS. 9, 10 and 11b have one edge that is square which will be placed on the posterior side of the lens capsule. The other edge (e.g., 10) can be filleted as it does not play a role in accommodation or PCO.

The haptic area can also be used to deliver drugs to the periphery of the lens capsule that can be used to prevent the proliferation of lens epithelial cells. Exemplary drugs can include antiproliferative drugs and anitiinflammatory drugs such as rapamycin and analogs thereof, such as sirolimus (also known as rapamycin), semi-synthetic derivatives of sirolimus (e.g., Zoltarilimus), everolimus and the like. Antimitotic drugs such as paclitaxel can also be used.

Materials comprising the lens can be polyolefins such as the thermoplastic poly(styrene-block-isobutylene-block-styrene) (SIBS), polyisobutylene, hydrogenated styrene-ethylenebutylene-styrene (SEBS), and the like. Alternatively, thermoset crosslinked polymers of the above can be used to provide enhanced memory to the polymers. Still alternatively, random copolymers of the above, crosslinked or non-crosslinked, comprised of monomers of isobutylene, monomers of styrene, monomers of crosslinker; for example 4-vinylbenxylcyclobutene, and the like. Alternatively the material comprising the lens can be silicone-based, such as silicone rubber poly(dimethylsiloxane), poly(diphenylsiloxane), poly(fluorosiloxane) or mixtures or co-polymers of the above; hydrogels such as poly(2-hydroxyethyl methacrylate) (pHEMA), polyacrylamide, poly(methylacrylamide), poly (vinyl pyrrilidinone), and the like; and other acrylics and acrylates and mixture and copolymers of all of the above. Any material can be used to form the lens that is biocompatible, biostable, non-inflammatory and that has an initial modulus less than 5 MPa, preferable less than 1,000 KPa, and preferably less than 600 KPa and greater than 100 KPa. If the lens is too soft, it risks extrusion anteriorly out of the capsulorrhexis, or in the event that the posterior capsule is removed, for example by a YAG laser to eliminate PCO, the lens should not extruded posteriorly. In addition, the material must have a refractive index greater than 1.33; preferably greater than 1.45, such that the optic can be made as thin as possible. The thinner the optic and the lower the modulus, the easier it is for the lens to stretch or compress along the plane of the optic by innervations of the ciliary muscles. The more the optic can stretch or compress and change its radius of curvature, and thickness, the higher the change in diopter.

The preferred material of the lens is a crosslinked polyolefin (more preferably, a crosslinked polyisobutylene) as described in U.S. Patent Publ. No. 2009/0124773, commonly assigned to assignee of the subject application and herein incorporated by reference in its entirety. The crosslinked polyolefin material of the lens includes a copolymer composition comprising a plurality of constitutional units that correspond to one or more branched alkene monomer species as well as a plurality of constitutional units that correspond to one or more olefin monomer species with pendant BCB groups. The copolymer composition can also include a plurality of constitutional units that correspond to one or more glass-forming monomer species. Typically, each of these constitutional units occurs within the copolymer molecule at a frequency of at least 2 times, and more typically at least 50, 100, 1000 or more times. Preferably, both the branched alkene monomer species and the olefin monomer species of the copolymer composition are cationically polymerizable.

The copolymer composition of the lens undergoes a crosslinking reaction at elevated temperatures (preferably above 180° C.). Due to the strained four-membered ring, benzocyclobutene (BCB) is converted to o-xylylene at temperatures above 180° C. At such elevated temperatures, the BCB group undergoes Diels-Alder reactions with dienophiles to form a six-membered ring, or reacts with itself to form an eight-membered ring. Polymers containing multiple pendant BCB groups per molecular chain can be thermally crosslinked with or without dienophiles. Each crosslink consists of a ring structure of carbon-carbon bond, which is more thermally stable than the sulfur bridge in vulcanized polymers and is stronger than the Si—O bond in silicone copolymers. The BCB crosslinking only involves heat. As long as the polymer is stable at the crosslinking temperature, there is no potentially toxic byproduct evolved.

In the preferred embodiment, the branched alkene monomer is both branched and contains a single double bond. The alkene monomer is also cationically polymerizable. Examples of suitable branched alkene monomers include $C_4$-$C_{14}$ branched alkenes such as isobutylene, 2-methyl-1-butene, 2-methyl-1-pentene, 2-methyl-1-hexene, beta-pinene, and combinations thereof. Preferably, the alkene monomer is a small-chain alkene, such as a $C_4$-$C_7$ alkene. More preferably, the branched alkene monomer is an isoolefin, such as isobutylene, 2-methyl-1-butene, 2-methyl-1-pentene, 2-methyl-1-hexene, and combinations thereof. Alkenes that are not cationically polymerizable, such as 1-hexene, cannot be added to the backbone of the polymer. Similarly, many dienes, such as 1,3-butadiene, cannot propagate in a cationic polymerization reaction, as the secondary carbon in the vinyl group will frequently cause the reaction to terminate. As such, dienes are typically only added to the backbone of a polymer as a cap or mono-addition to a living end. See De et al., "Relative Reactivity of C4 Olefins toward the Polyisobutylene Cation," *Macromolecules,* 39 (2006) pp. 6861-70. Additionally, effective cationic polymerization can be difficult using dienes having sterically hindered tertiary carbons.

In the preferred embodiment, the olefin monomer having a pendant BCB group is cationically polymerizable and compatible with the branched alkene monomer. Suitable olefin monomers having a pendant BCB group include 4-vinylbenzocyclobutene, 4-(α-alkylvinyl)benzocyclobutenes such as 2-(4-benzocyclobutenyl)-propene and 2-(4-benzocyclobutenyl)-1-butene, and 4-(2-methyl-alkenyl)benzocyclobutenes such as 2-methyl-3-(4-benzocyclobutenyl)-1-propene and 2-methyl-4-(4-benzocyclobutenyl)-1-butene.

Preferred olefin monomers having a pendant BCB group have the formula wherein R is hydrogen or an alkyl group (preferably methyl, ethyl, or propyl) and n is 0. Examples of this type of preferred olefin monomer include 4-vinylbenzocyclobutene and 2-(4-benzocyclobutenyl)-propene.

Preferred olefin monomers having a pendant BCB group also include compounds having the same formula but wherein R is an alkyl group (preferably methyl, ethyl, or propyl) and n is an integer ranging from 0-3. Examples of this type of preferred olefin monomers include 4-vinylbenzocyclobutene, 2-(4-benzocyclobutenyl)-propene, 2-methyl-3-(4-benzocyclobutenyl)-1-propene, and 2-methyl-4-(4-benzocyclobutenyl)-1-butene.

Examples of suitable glass-forming monomers include styrenic monomers such as styrene, alpha-alkyl styrene (e.g., alpha-methyl styrene), 4-alkylstyrene, 4-alkoxystyrene, and various benzene-ring substituted styrenes. Suitable glass-forming monomers also include non-reactive glassy compounds such as norbornadiene or norbornene. The non-reactive glassy compounds are preferably bicyclic bridged systems that obey Bredt's rule, which states that the bridgeheads cannot be involved in a double bond. Compounds falling under this rule are typically inert. Preferably, the glass-forming monomer is styrene.

Additional olefins that are cationically polymerizable may also added to the copolymer composition. For instance, the polymer may contain a plurality of constitutional units that include 1,3-dienes, vinyl ethers, N-vinyl ethers, N-vinyl carbazoles, N-vinyl pyrrolidone, aldehydes, ketones, or combinations thereof. An embodiment of this invention is directed towards a polymer in which the alkene component is copolymerized with one or more 1,3-dienes. Preferred 1,3-dienes include isoprene and 1,3-butadiene. Because the 1,3-dienes cannot be homopolymerized by cationic polymerization, it is preferable that they are copolymerized with isobutylene or another suitable branched alkene.

The cationically polymerizable branched alkene monomer preferably contains a tertiary carbon on the vinyl group in the alkene. As known by those of skill in the art, cations are stable on the tertiary carbon due to the electron-donicity of the surrounding carbons that stabilize the positive charge of the cation. Polyisobutylene is an example of a branched alkene monomer polymerizable by cationic chemical means that contains a tertiary carbon. Molecules such as propene contain secondary carbons at the vinyl group and, as known by those of skill in the art, are not cationically polymerized.

The copolymer composition of the lens material of the present invention embrace a variety of configurations, for example, cyclic, linear and branched configurations. Branched configurations include star-shaped configurations (e.g., configurations in which three or more chains emanate from a single region), comb configurations (e.g., graft copolymers having a main chain and a plurality of side chains), and dendritic configurations (including arborescent or hyperbranched copolymers). The copolymer composition of the lens material of the present invention embrace (a) copolymers comprising one or more chains containing repeating constitutional units of a single type (e.g., block copolymers), (b) copolymers comprising one or more chains containing randomly distributed constitutional units of two or more types (e.g., random copolymers), (c) copolymers comprising one or more chains containing two or more types of constitutional units that repeat within an ongoing series (e.g., alternating copolymers), such as triblocks, quadblocks, and so forth.

For example, in certain beneficial embodiments, the copolymer composition of the lens material of the present invention are random copolymers containing (a) one or more alkene monomer units, which contain a plurality of units corresponding to one or more branched alkene monomer species and (b) one or more BCB-olefin monomer units, which contain a plurality of units corresponding to one or more BCB-olefin monomer species. Examples of branched alkene monomer species and BCB-olefin monomer species are discussed above.

For another example, in certain beneficial embodiments, the copolymer composition of the lens of the present invention are block copolymers containing (a) one or more olefin monomer blocks, which contain a plurality of units corresponding to one or more branched alkene monomer species and (b) one or more BCB-olefin monomer blocks, which contain a plurality of units corresponding to one or more BCB-olefin monomer species. Examples of branched alkene monomer species and BCB-olefin monomer species are discussed above. As above, in some embodiments, the BCB-olefin blocks can further contain a plurality of units that correspond to glass-forming monomer species.

Those skilled in the art would also appreciate that the material used in a lens can contain an ultraviolet blocking agent that would block out ultraviolet light below a wavelength of 400 nm. The ultraviolet blocking agent can be bonded into the backbone of the polymer or incorporated into the polymer by means of covalent bonds formed during the crosslinking step upon forming a thermoset. In addition, an ultraviolet blocking agent can simply be blended into the polymer prior to polymerization.

The number average molecular weight (Mn) of the block copolymers of the present invention typically range, for example, from about 1000 to about 2,000,000, more typically from about 10,000 to about 300,000, even more typically 40,000 to 100,000, with the BCB-olefin units typically comprising 0.01-60 mol %, more typically 0.5-40 mol %, even more typically 0.5-7 mol % of the polymer. In some embodiments, polymers have a narrow molecular weight distribution such that the ratio of weight average molecular weight to number average molecular weight (Mw/Mn) (i.e., the polydispersity index) of the polymers ranges from about 1.0 to about 2.5, or even from about 1.0 to about 1.4.

In the preferred embodiment, both the branched alkene monomer species and the olefin monomer species of the copolymer composition are polymerizable by living cationic polymerization. Living polymerization is a polymerization that proceeds in the practical absence of chain transfer and termination. It is a desirable objective in polymer synthesis. Living cationic polymerization implies that a polymer can be grown from one or from a plurality of active sites in a controlled manner (controlled molecular weight, molecular weight distribution, end functionalities, etc.). During this growth process, different molecules can be incorporated into the backbone of the polymer, yielding polymers with well-defined structures. In other embodiment, other synthesis techniques can be used as described in U.S. Patent App. Publ. No. 2009/0124773.

In the preferred embodiment, the polyolefin copolymer of the lens is formed at low temperature from a reaction mixture that comprises: (a) a solvent system appropriate for cationic polymerization, (b) one or more branched alkene monomer species, (c) an initiator, and (d) a Lewis acid coinitiator. In addition, a proton-scavenger is also typically provided to ensure the practical absence of protic impurities, such as water, which can lead to undesirable reaction byproducts in the final product. An inert nitrogen or argon atmosphere is generally required for the polymerization.

Polymerization can be conducted, for example, within a temperature range of from about 0° C. to about −100° C., more typically from about −50° C. to −90° C. Polymerization times are typically those times that are sufficient to reach the desired conversion.

Among the solvent systems appropriate for cationic polymerization, many of which are well known in the art, are included: (a) $C_1$-$C_4$ halogenated hydrocarbons, such as methyl chloride and methylene dichloride, (b) $C_5$-$C_8$ aliphatic hydrocarbons, such as pentane, hexane, and heptane, (c) $C_5$-$C_{10}$ cyclic hydrocarbons, such as cyclohexane and methyl cyclohexane, and (d) mixtures thereof. For example, in some beneficial embodiments, the solvent system contains a mixture of a polar solvent, such as methyl chloride, methylene chloride and the like, and a nonpolar solvent, such as hexane, cyclohexane or methylcyclohexane and the like.

Initiators for living carbocationic polymerization are commonly organic ethers, organic esters, organic alcohols, or organic halides, including tert-ester, tert-ether, tert-hydroxyl and tert-halogen containing compounds. Specific examples include alkyl cumyl ethers, such as dicumyl ether and tricumyl ether; cumyl halides, alkyl cumyl esters, cumyl hydroxyl compounds and hindered versions of the same, for instance, dicumyl chloride, 5-tert-butyl, 1,3-dicumyl chloride, and 5-tert-butyl-1,3-bis(1-methoxy-1-methylethyl)benzene. 5-tert-butyl-1,3-bis(1-methoxy-1-methylethyl)benzene and 1,3,5 tricumyl ether are the preferred initiators for cationic polymerization and may be prepared through the methods disclosed in Wang B. et al., "Living carbocationic polymerization XII. Telechelic polyisobutylenes by a sterically hindered bifunctional initiator" Polym. Bull. (1987)17: 205-11; or Mishra M. K., et al., "Living carbocationic polymerization VIII. Telechelic polyisobutylenes by the MeO $(CH_2)_2C$-p-$C_5H_4$—$C(CH_3)_2$ OMe/$BCl_3$ initiating system" Polym. Bull. (1987) 17:7-13, both of which are herein incorporated by reference in their entirety. The initiators used for crosslinkable polyolefins described in this invention include mono or multifunctional initiators.

Carbocationically terminated star polymers can be formed by selecting initiators having three or more initiation sites, for example, tricumyl chloride (i.e., 1,3,5-tris(1-chloroy-1-methylethyl)benzene) and tricumyl ether which contain three initiation sites.

Examples of Lewis acid coinitiators include metal halides such as boron trichloride, titanium tetrachloride and alkyl aluminum halides. The Lewis acid coinitiator is typically used in concentrations equal to or greater, e.g., 2 to 50 times greater, than the concentration of the initiator.

Examples of proton-scavengers (also referred to as proton traps) include substituted or unsubstituted 2,6-di-tert-butylpyridines, such as 2,6-di-tert-butylpyridine and 4-methyl-2,6-di-tert-butylpyridine, as well as 1,8-bis(dimethylamino)-naphthalene and diisopropylethyl amine. The concentration of the proton trap is preferably only slightly higher than the concentration of protic impurities such as water in the polymerization system.

Further information regarding the preparation of block copolymers from monomer species that have significantly different reactivities can be found, for example, in US Patent Appl. Publ. No. 2005/0187414, herein incorporated by reference in its entirety.

Allyltrimethylsilane can be added to the reaction mixture to terminate (end-cap) the ends of the polymer with allyl groups, thereby eliminating the chlorine atom that typically resides on the end of the cationically polymerized polymer chain. Chlorine was found to dissociate at high temperature and corrode molds or extrusion equipment. In addition it was found to be extremely hygroscopic as it resides in the form of HCl and thereby brings water into the matrix which manifests as clouding.

Non-reacted plasticizers can be added to the crosslinked polyolefin material if desired. Examples of such plasticizers include polyisobutylene of molecular weight 500 to 10,000 Daltons (more preferably from 500 to 1500 Daltons).

In the preferred embodiment, the crosslinked polyolefin material of the accommodating intraocular lens of the present invention is a long chain polymer with 10,000 to 100,000 Daltons between crosslinks (with 50,000 to 90,000 Daltons between crosslinks most preferred). The number of Daltons (or the molecular weight) between crosslinks, which is also commonly referred to as crosslinked density, can be controlled in several manners. One method is to dilute the crosslinker in a solvent that is compatible with the reaction bath, such as methycyclohexane, and adding the solution in tandem with the addition of monomers comprising the backbone of the polymer. If the crosslinker is comprised, for example of a 10% concentration of crosslinker in methycyclohexane, the crosslink density would be ten times greater than a similar solution where the crosslink concentration was 1%. Another method of controlling the crosslink density is to add the crosslinker sequentially with the monomers comprising the backbone; for example, one-quarter of the backbone of the polymer can be added and then reacted for a certain amount of time, at which point one-quarter of the crosslinker is added. This sequence is repeated until all of the reactants are consumed. In the preferred embodiment, the crosslinked polyolefin material of the accommodating intraocular lens of the present invention employs a 1 to 4 percent by weight of 4-vinylbenzycyclobutene as the crosslinker component.

For the non-accommodating intraocular lens of the present invention, the crosslinked polyolefin material of the accommodating intraocular lens crosslinked polyolefin material of the lens includes more glassy segments and are therefore harder and with higher modulus than lenses that are designed for accommodation. Non-accommodating lenses will have styrene contents in the order of 10 to 35 mole percent. Accommodating lenses will have styrene contents less than 10 percent and preferably devoid entirely of styrene. The crosslink density can also be used to control modulus of the polymer where the less crosslink density, the softer the polymer. In the preferred embodiment, the crosslinked polyolefin material of the non-accommodating intraocular lens of the present invention employs a 4 to 10 percent by weight of 4-vinylbenzycyclobutene as the crosslinker component.

The polyolefin copolymer of the lens as described herein makes an excellent elastomer which can either be thermoplastic or thermosetting depending upon whether a crosslinker is employed and if employed, whether or not it is crosslinked thereafter. However, prior to forming the lens, it should be subjected to a cleaning and purification procedure (FIG. 19) to improve the in vivo transparency of the end product lens. The polyolefin copolymer can then be molded or extruded or cast into its desired lens form and then heat cured to react the olefin having the pendant BCB group with itself to crosslink the polymer into a thermoset shape. Alternatively, the crosslinking can be accomplished by molding the lens at temperatures that thermally activate the crosslinking of the pendant BCB group. The resultant lens product provides better heat stability, better creep resistance, less water uptake, and less swelling or solubility in organic solvents.

The invention is further described with reference to the following non-limiting examples.

EXAMPLE 1

Synthesis of poly(st-co-4VBCB)-polyIB-poly(st-co-4VBCB) triblock copolymer 337 mL of methylcyclohexane (MeCHx) were added to a glass reaction vessel equipped with a mechanical stirrer, stainless steel serpentine tubing for liquid nitrogen cooling, stainless steel tubing for feeding methyl chloride (MeCl) and isobutylene (IB) into the vessel, a thermocouple with temperature controller, a nitrogen bubbler and an addition dropping funnel. The liquid was cooled down to –80° C. by liquid nitrogen cooling. Sequentially MeCl (189 g) and IB (20 g) were added through the feeding line immersed in the liquid, so that the gases are condensed into the liquid. While gases were being condensed, an initiator solution (HDCE/DTBP/MeCHx 0.28 g/0.45 mL/15 mL) was added through a port on the reactor lid. TiCl$_4$ (3.5 mL) was then added through an opening in the reactor lid, which started the IB polymerization (the timer is started). Forty minutes later, a sample of ~4 mL of reaction mixture was withdrawn from the reactor and quenched in excess methanol. A mixture of styrene/4VBCB/MeCHx (7 mL/2 mL/20 mL) was added slowly into the reactor through a syringe over 2 minutes. After 6 minutes, the reaction was quenched with excess methanol.

The reaction mixture was stored under the fume hood overnight. The top layer was separated and washed repeatedly with distilled water until neutral. The solution was precipitated into isopropyl alcohol, followed by dissolution in toluene and precipitation in isopropyl alcohol again. The precipitate was dried in a vacuum oven at ~60° C. until constant weight was obtained (yield: 22 g).

The polymer was characterized by GPC and NMR. Both the starting PIB (low elution volume) and the triblock copolymer (high elution volume) show a narrow monodispersed peak in GPC RI traces, and the traces shift smoothly as molecular weight increases. In addition, there is a singlet at ~3.1 ppm in proton NMR spectrum, which is attributed to the strained ring of BCB. The broad peaks at ~6.4-7.3 ppm are attributed to aromatic protons on styrene and 4-VBCB monomer units. From the relative integration intensities, the copolymer was determined to have ~3 mol % 4-VBCB and ~7 mol % styrene. When heated up to 240° C. for 10 min, the copolymer became insoluble in THF and thus thermally crosslinked.

EXAMPLE 2

Synthesis of poly(IB-co-4VBCB) Random Copolymer 337 mL of methylcyclohexane (MeCHx) were added to a glass reaction vessel equipped with a mechanical stirrer, stainless steel tubing for liquid nitrogen cooling, stainless steel tubing for feeding methyl chloride (MeCl) and isobutylene (IB) into the vessel, a thermocouple with temperature controller, a nitrogen bubbler and an addition dropping funnel. The liquid was cooled down to –80° C. by liquid nitrogen cooling. Sequentially MeCl (189 g) and IB (5 g) were added through the feeding line immersed in the liquid, so that the gases are condensed into the liquid. While gases are being condensed, an initiator solution (HDCE/DTBP/MeCHx 0.28 g/0.45 mL/15 mL) was added through a port on the reactor lid. TiCl$_4$ (3.5 mL, using a 10 cc glass syringe) was then added through an opening in the reactor lid, which starts the IB polymerization (the timer was started). Five minutes later, 36 g of IB and 1.5 g 4VBCB (dissolved in 10 mL of MeCHx) were added slowly, taking 7 min and 9.5 min, respectively. After all 4-VBCB was added, the reaction is continued for 60 min. Samples were taken at 5, 30 and 60 min. The reaction was quenched with excess methanol in the end.

The reaction mixture was stored under the fume hood overnight. The top layer was separated and washed repeatedly with distilled water until neutral. The solution was precipitated into isopropyl alcohol, followed by dissolution in hexane and precipitation in isopropyl alcohol again. The precipitate was dried in a vacuum oven at ~60° C. until constant weight (yield: 35 g).

The polymer was characterized by GPC and proton NMR. GPC RI traces of the samples show that the molecular weight increases with reaction time. Little change was observed in molecular weight (~10%) from 30 min to 60 min, as the polymerization approached completion. Each sample had a UV signal with similar elution volume as its RI signal. The sample taken at 5 min exhibited a much stronger UV signal than the other two, indicating that it has a higher 4-VBCB content at lower conversion. The incorporation of 4-VBCB into the copolymer was further confirmed by proton NMR spectroscopy. A singlet at ~3.1 ppm was seen in proton NMR spectrum, which is attributed to the strained ring of BCB. When heated up to 240° C. for 10 min, the copolymer became insoluble in THF and thus thermally crosslinked.

EXAMPLE 3

Synthesis of poly(IB-co-4VBCB) Random Copolymer 0.53 g of Tricumyl ether (TCE) and 0.51 mL of di-t-butyl pyrilidone DTBP were predissolved in ~30 mL of methylcyclohexane (MeCHx) and added to a stainless steel reaction vessel equipped with a mechanical stirrer and a prechiller.

1,000 mL of MeCHx was added to the reaction vessel. Under nitrogen atmosphere, the liquid solution in the reaction vessel was mixed using the mechanical stirrer. Liquid nitrogen was used to cool the reaction vessel to −80° C. (used a temperature controller, a thermocouple and a solenoid valve). 567 g of Methyl Chloride (MeCl) and 110 g of isobutylene (IB) were condensed in the prechiller and added to the reaction vessel. Titanium tetrachloride ($TiCl_4$) was then added to start the polymerization of the IB.

Five minutes after the addition of $TiCl_4$, a solution of 5.4 ml of 4-vinylbenzenecyclobutene (4VBCB), 0.1 g of DTBP, and 15.4 mL of MeCHx was added to the reaction vessel via a syringe pump at 1 mL/min.

Sixty minutes after the addition of $TiCl_4$, a solution of 4.0 g of allyltrimethylsilane (ATMS), 0.1 g of DTBP, and 20 mL of MeCHx was added slowly to the reaction mixture. ATMS is added to the reaction to terminate (end-cap) the ends of the polymer with allyl groups thereby eliminating the chlorine atom that typically resides on the end of the cationically polymerized polymer chain. Chlorine was found to dissociate at high temperature and corrode molds or extrusion equipment. In addition it was found to be extremely hygroscopic as it resides in the form of HCl and thereby brings water into the matrix which manifests as clouding.

One hour after addition of ATMS mixture, the reaction was quenched by the addition of ~150 mL of methanol (MeOH). The reaction mixture was poured from the reaction vessel to a 2 L glass beaker and warmed up to room temperature.

Subsequent thereto, the reaction mixture stored in the glass beaker was subjected to the cleaning and purification procedure as described below with respect to FIG. 19.

Subsequent to the cleaning and purification procedure, sample disks were made by placing ¼ g of the polymer product between two glass slides and then compression molding the slides/polymer in a compression molding machine at 240° C. for 30 minutes. The 240° C. temperature of the molding operations operates to crosslink the polymer because it is greater than the activation temperature (~180° C.) of the crosslinking agent (4VBCB). The slides/polymers were cooled and the polymer punched into circular disks using a circular punch. Approximately 20 disks made in this manner were incubated at 50° C. for one week and examined for cloudiness. All samples were optically clear with no observable haziness or cloudiness reported at one week.

EXAMPLE 4

Thermal crosslinking of
poly(st-co-4VBCB)-polyIB-poly(st-co-4VBCB)
triblock copolymer A sample (0.2 g) of the poly(st-co-4VBCB)-polyIB-poly(st-co-4VBCB) triblock copolymer as formed above was placed between two Teflon films, and the films placed between two flat metal plates. The resulting structure was placed in a hot press (250° C.) for 10 minutes with virtually no pressure applied. The Teflon films with the polyolefin sample were removed from the plates and cooled to room temperature. A small piece of the heat treated polymer was placed in a vial containing THF. The film remained insoluble overnight and longer, indicating that it crosslinked.

Polymer samples were thermally treated at different temperatures for 10 minutes. At temperatures above 220° C., the resultant polymer is insoluble in THF. At a temperature of 200° C., the resultant polymer is soluble in THF. For thermal crosslinking below 220° C., extended time periods (>10 min) are necessary.

EXAMPLE 5

Preparation of a SIBS Triblock Polymer

SIBS was prepared in two steps in one pot. In the first step, isobutylene was polymerized by a 5-tert-butyl, 1,3-dicumyl chloride/$TiCl_4$ initiating system in a methyl chloride/hexanes solvent system in the presence of a proton trap under a blanket of dry nitrogen at −80° C. When the central PIB block reached the desired molecular weight, in this case 50 KDaltons, a sample was removed from the reactor and styrene was added to the reactor and the polymerization continued until the outer polystyrene blocks also reached a predetermined length, in this case 75 KDaltons. The process was terminated by the addition of methanol. The sample that was taken was dried in an oven. After drying in the oven, the sample was observed to have a consistency similar to that of a rubber band.

EXAMPLE 6

Comparative Example Using 1-hexene

This experiment was run to compare the effect of polyisobutylene, as described in Example 5, with 1-hexene. 1-hexene was dissolved in a methyl chloride/hexanes solvent system and the mixture was added to the reaction pot in the presence of a 5-tert-butyl, 1,3-dicumyl chloride/$TiCl_4$ initiating system, also in a methyl chloride/hexanes solvent system, in the presence of a proton trap under a blanket of dry nitrogen at −80° C. However, in this case, at the end of the addition, a sample was taken which when dry, resembled a lumpy oil. The reaction never went to completion because of chain termination effects. The styrene was never added to the reactor as the experiment was aborted.

Based on these results, it was concluded that 1-hexene could not achieve an elastomer by cationic polymerization. Instead, the reaction produced low molecular weight oils.

Figure 19:
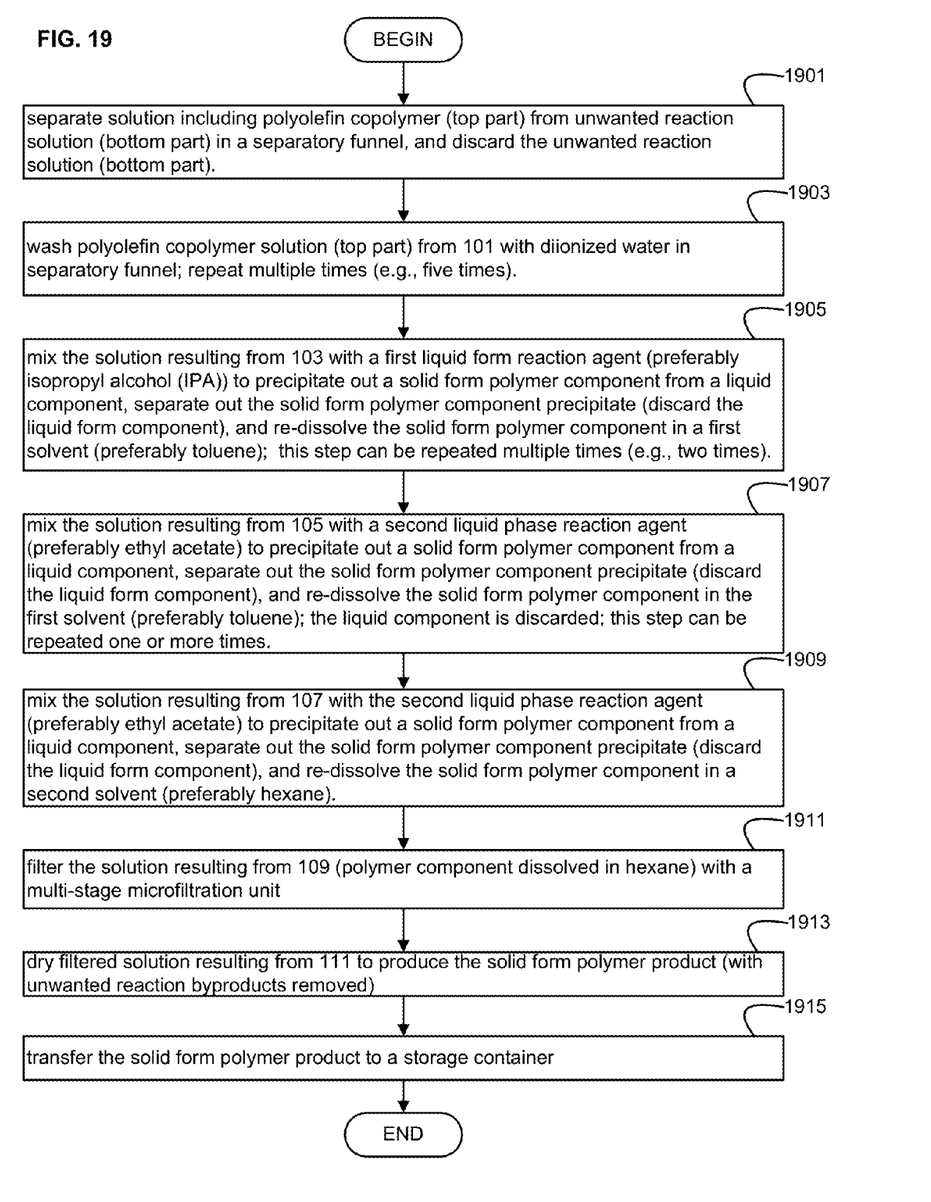
FIG. 19 is a flow chart illustrating cleaning operations for removing unwanted reaction byproducts from a polyolefin copolymer material to improve the in vivo transparency of resulting lens device formed therefrom.

In the preferred embodiment, the polyolefin copolymer as described herein is subject to a cleaning and purification procedure as shown in FIG. 19 to reduce unwanted reaction byproducts in the polyolefin copolymer that if left intact reduce the in vivo transparency of the end product lens. The resultant polyolefin copolymer can then be molded or extruded or cast into its desired lens form and then heat cured to react the olefin having the pendant BCB group with itself to crosslink the polymer into a thermoset shape. Alternatively, the crosslinking can be accomplished by molding the lens at temperatures that thermally activate the crosslinking of the pendant BCB group. The resultant lens formed from the clean polymer provides improved in vivo transparency, particularly over long time durations implanted within the ocular fluids of the eye.

The cleaning procedure begins in step 1901 wherein the liquid form polyolefin reaction product is added to a separatory funnel that partitions the reaction product into two immiscible phases. The top part is a solution containing the polyolefin copolymer and the bottom part is an aqueous-based unwanted reaction solution comprised of methanol, methoxy salts of titanium and other water soluble molecules. The bottom part is discarded to leave behind the polyolefin copolymer solution.

In step 1903, the polyolefin copolymer solution extracted in 1901 is washed in diionized water in the separatory funnel.

This step is preferably repeated multiple times (e.g., five times) to remove more salts, methanol, and other water soluble impurities.

In step 1905, the polyolefin copolymer solution resulting from step 1903 is mixed with a first liquid form reaction product (preferably a polar solvent such as isopropyl alcohol) to precipitate out a solid form polymer component from a liquid component. The solid form polymer component includes the polyolefin copolymer as described herein. The precipitate (the solid form polymer component) is separated out from the liquid component (the liquid form component is discarded) and the precipitate (the solid form polymer component) is re-dissolved in a first non-polar solvent (preferably toluene). This step can be repeated multiple times (e.g., two times). This serial dissolution in non-polar solvent and precipitation in polar solvent removes low molecular weight unreacted monomers, such as styrene as well as low molecular weight oligomers.

In step 1907, the polyolefin copolymer solution resulting from step 1905 is mixed with a second liquid form reaction product (different than the first liquid form reaction product, and preferably ethyl acetate) to precipitate out a solid form polymer component from a liquid component. The solid form polymer component includes the polyolefin copolymer as described herein. The precipitate (the solid form polymer component) is separated out from the liquid component (the liquid form component is discarded) and the precipitate (the solid form polymer component) is re-dissolved in the first solvent (preferably toluene). This step can be repeated one or more times. In the preferred embodiment, this step 1907 uses a more specific polar solvent, i.e., ethyl acetate to remove the homopolymer of the crosslinker (i.e., 4VBCB) and/or of the styrene component from the precipitate; both of which if present can impart cloudiness to the lens formed thereafter.

In step 1909, the polyolefin copolymer solution resulting from step 1907 is mixed with the second liquid form reaction product (preferably ethyl acetate) to precipitate out a solid form polymer component from a liquid component. The solid form polymer component includes the polyolefin copolymer as described herein. The precipitate (the solid form polymer component) is separated out from the liquid component (the liquid form component is discarded) and the precipitate (the solid form polymer component) is re-dissolved in a solvent (preferably hexane). The solvent (e.g., hexane) provides a media where any remaining homopolymer of the crosslinker (e.g., 4VBCB) and/or of the styrene remains suspended. If homopolymer is still present, the solution looks cloudy. If homopolymer is absent, the solution in hexane is crystal clear. Further, if the solution is cloudy, which is indicative of homopolymer of crosslinker or polystyrene, this suspension is easier to filter than a similar solution using toluene as the solvent, as the homopolymer is very soluble in toluene and will generally pass through the filter system of step 1911.

In step 1911, the solution resulting from step 1909 (which includes the polyolefin copolymer dissolved in hexane) is filtered by a multi-stage microfiltration unit. Each respective stage of the filtration process removes unwanted reaction byproducts from the solution by passage through a microporous membrane. In the preferred embodiment, the multi-stage microfiltration unit employs a sequence of stages that operate to filter out particulates with maximal dimensions greater than the smallest wavelength of visible light (around 390 nm or 0.39 µm). In an exemplary embodiment, the multi-stage microfiltration unit employs a sequence of seven stages. The first stage employs a stainless steel filter membrane with a pore size of 2 µm. The second stage employs a sintered stainless steel filter membrane with a pore size of 0.5 µm. The third stage employs a glass fiber filter membrane with a pore size of 0.1 µm. The fourth stage (which is the same as the third stage) employs a glass fiber filter membrane with a pore size of 0.1 µm. The fifth stage employs a PTFE filter membrane with a pore size in a range between 0.1 µm to 0.3 µm (more preferably on the order of 0.2 µm). The sixth stage employs a PTFE filter membrane with a pore size in a range between 0.1 µm to 0.3 µm (more preferably on the order of 0.2 µm). The seventh stage employs a PTFE filter membrane with a pore size in a range between 0.1 µm to 0.3 µm (more preferably on the order of 0.2 µm). The filter system effectively removes remaining unwanted reaction byproducts such as titanium dioxide (which is the product of titanium tetrachloride and water) as well as any crystals of homopolymer of 4-vinylbenzylcyclobutene or polystyrene.

In step 1913, the filtered solution resulting from step 1911 is dried for several hours at 100° C. to 130° C. to produce a solid form polymer product. For example, when applying the cleaning and purification process to the polymer reaction product of Example 3, the solid form polymer product produced in 1913 includes the allyl-end-capped polyolefin copolymer with unwanted components removed therefrom. Such unwanted components include, hydrochloric acid, titanium tetrachloride, methoxy salts of titanium, titanium dioxide, other salts of titanium, residual scavenger, unreacted reactants, such as styrene, 4-vinylbenzylcyclobutene, homopolymer of styrene, homopolymer of 4-vinylbenzylcyclobutene, oligomer and trace solvents, as describe above. Removing such unwanted components significantly reduces clouding (decrease in transparency) of the resulting lens structure in the in vivo ocular environment over time as can be simulated by incubating the lens in saline at 50° C. for several weeks.

In step 1915, the solid form polymer product resulting from step 1913 is transferred to a storage container for subsequent use.

There have been described and illustrated herein several embodiments of an intraocular lens for implantation into the human eye as well as preferred materials and methods for fabricating intraocular lens. While particular embodiments of the invention have been described, it is not intended that the invention be limited thereto, as it is intended that the invention be as broad in scope as the art will allow and that the specification be read likewise. For example, while the copolymer materials described herein are particularly suited for accommodating lens designs, such materials can be used for non-accommodating intraocular lens as well as other lens devices such as a corneal lens implant and contact lens. Moreover, the polymer purification process as described herein can readily be adapted for other lens polymer systems in order to remove unwanted reaction byproducts that contribute to clouding (decrease in transparency) of the resulting lens structure in the in vivo environment over time. It will therefore be appreciated by those skilled in the art that yet other modifications could be made to the provided invention without deviating from its spirit and scope as described herein.

We claim:
1. A method of making a refractive optics structure comprising:
  a) processing a polyolefin copolymer material to remove unwanted reaction byproducts that can contribute to reduced transparency of the polyolefin copolymer material in the ocular environment of the eye during use, said unwanted reaction byproducts selected from the group including
    i) homopolymers of a crosslinking component of the polyolefin copolymer material, ii) homopolymers of a glass-forming component of the polyolefin copolymer material,
iii) water-soluble and non-water-soluble particles of a predetermined size corresponding to the characteristic wavelength range of visible light as well as water-soluble and non-water-soluble particles greater than said predetermined size; and
b) forming the refractive optics structure from the polyolefin copolymer material processed in a), wherein the forming involves thermal activation of said crosslinking component of said polyolefin copolymer material in order to crosslink said polyolefin copolymer material;
wherein the processing of a) involves
A) precipitating polyolefin copolymer material in at least one solution that includes a polar solvent,
B) dissolving the polyolefin copolymer material precipitated in A) in a solution that includes a non-polar solvent, and
C) filtering of the solution of B) with the polyolefin copolymer material dissolved therein in a number of successive filtering stages.

2. A method according to claim 1, wherein:
the precipitating of A) is repeated for multiple iterations that employ different solutions with different polar solvents.

3. A method according to claim 1, wherein:
activation of said crosslinking component is performed subsequent to compression molding by heat curing of the molded product produced by compression molding.

4. A method according to claim 2, wherein:
at least one iteration of the multiple iterations employs a first solution with a polar solvent that operates to remove homopolymers of the crosslinking component of the polyolefin copolymer material.

5. A method according to claim 4, wherein:
the polar solvent of the first solution includes ethyl acetate.

6. A method according to claim 2, wherein:
at least one iteration of the multiple iterations employs a second solution with a polar solvent that operates to remove homopolymers of the glass-forming component of the polyolefin copolymer material.

7. A method according to claim 1, wherein:
the non-polar solvent of the solution of B) allows for homopolymers of the crosslinking component of the polyolefin copolymer material to remain suspended in the solution of B) for removal by the filtering of C).

8. A method according to claim 7, wherein:
at least one filtering stage employed in C) includes a filter membrane having a specified pore size in a range between $0.1\mu m$ to $0.3\mu m$.

9. A method according to claim 8, wherein:
the specified pore size is $0.2\mu m$.

10. A method according to claim 8, wherein:
the filter membrane is realized from PTFE.

11. A method according to claim 1, wherein:
the refractive optics structure has a radius of curvature that varies according to accommodating forces applied by the ciliary muscles of the ocular environment.

12. A method according to claim 1, wherein:
the refractive optics structure is non-accommodating with a fixed radius of curvature that does not vary according to accommodating forces applied by the ciliary muscles of the ocular environment.

13. A method according to claim 1, wherein:
the polyolefin copolymer material comprises
A) a plurality of constitutional units that include at least one cationically polymerizable isoolefin selected from the group consisting of isobutylene, 2-methyl-1-butene, 2-methyl-1-pentene, 2-methyl-1-hexene, and combinations thereof;
B) a plurality of constitutional units that include at least one cationically polymerizable olefin monomer having a pendant benzocyclobutene (BCB) group, wherein said olefin monomer having a pendant benzocyclobutene (BCB) group comprises the crosslinking component of the polyolefin copolymer material; and
optionally
C) a plurality of constitutional units that include at least one glass-forming monomer.

14. A method according to claim 13, wherein:
said isoolefin of A) is isobutylene.

15. A method according to claim 13, wherein:
said olefin monomer having a pendant BCB group of B) is 4-vinylbenzocyclobutene or 2-(4-benzocyclobutenyl)-propene.

16. A method according to claim 13, wherein:
said glass-forming monomer of C) is present and selected from the group consisting of styrene, indene, α-methylstyrene, p-tert-butylstyrene, p-chlorostyrene, p-methoxystyrene, p-tert-butoxystyrene, p-hydroxystyrene, norbornene, and combinations thereof.

17. A method according to claim 13, wherein:
the polyolefin copolymer material is synthesized using dicumyl ether or tricumyl ether as an initiator molecule and isobutylene that is randomly polymerized with 4-vinylbenzocyclobutene.

18. A method according to claim 17, wherein:
the polyolefin copolymer material includes allyl end groups.

19. A method according to claim 18, wherein:
the polyolefin copolymer material includes a component that absorbs or otherwise blocks ultraviolet light.

20. A method according to claim 1, wherein:
the crosslinking component of the polyolefin copolymer material comprises 4-vinylbenzocyclobutene.

21. A method according to claim 1, wherein:
the glass-forming component of the polyolefin copolymer material comprises styrene.

22. A method of making a refractive optics structure comprising:
a) processing a polyolefin copolymer material having a crosslinking component, the processing removing unwanted reaction byproducts that can contribute to reduced transparency of the polyolefin copolymer material in the ocular environment of the eye during use; and
b) forming the refractive optics structure from the polyolefin copolymer material processed in a), wherein the forming involves activation of said crosslinking component of said polyolefin copolymer material in order to crosslink said polyolefin copolymer material;
wherein the processing of a) involves
A) precipitating polyolefin copolymer material in at least one solution that includes a polar solvent,
B) dissolving the polyolefin copolymer material precipitated in A) in a solution that includes a non-polar solvent, and
C) filtering of the solution of B) with the polyolefin copolymer material dissolved therein in a number of successive filtering stages.

23. A method according to claim 22, wherein:
at least one of the filtering stages employed in C) includes a filter membrane having a specified pore size in a range between $0.1\mu m$ to $0.3\mu m$.

24. A method according to claim 23, wherein:
the specified pore size is 0.2µm.

25. A method according to claim 23, wherein:
the filter membrane is realized from PTFE.

26. A method according to claim 22, wherein:
the precipitating of A) is repeated for multiple iterations that employ different solutions with different polar solvents.

27. A method according to claim 26, wherein:
said unwanted reaction byproducts include homopolymers of the crosslinking component of the polyolefin copolymer material; and
at least one iteration of the multiple iterations employs a first solution with a polar solvent that operates to remove the homopolymers of the crosslinking component of the polyolefin copolymer material.

28. A method according to claim 27, wherein:
the polar solvent of the first solution includes ethyl acetate.

29. A method according to claim 26, wherein:
said unwanted reaction byproducts include homopolymers of a glass-forming component of the polyolefin copolymer material; and
at least one iteration of the multiple iterations employs a second solution with a polar solvent that operates to remove homopolymers of the glass-forming component of the polyolefin copolymer material.

30. A method according to claim 22, wherein:
the non-polar solvent of the solution of B) comprises hexane.

31. A method according to claim 22, wherein:
said forming of b) involves compression molding of the polyolefin copolymer material within a compression mold.

32. A method according to claim 31, wherein:
activation of said crosslinking component is performed subsequent the compression molding by heat curing of the molded product produced by compression molding.

33. A method according to claim 22, wherein:
said unwanted reaction byproducts selected from the group including
  i) homopolymers of a crosslinking component of the polyolefin copolymer material,
  ii) homopolymers of a glass-forming component of the polyolefin copolymer material, and
  iii) water-soluble and non-water-soluble particles of a predetermined size corresponding to the characteristic wavelength range of visible light as well as water-soluble and non-water-soluble particles greater than said predetermined size.

* * * * *